United States Patent [19]
Heinonen

[11] Patent Number: 5,748,304
[45] Date of Patent: May 5, 1998

[54] MEASURING INSTRUMENT FOR REFLECTOMETRIC MEASUREMENTS

[75] Inventor: Aimo Heinonen, Espoo, Finland

[73] Assignee: Conrex Automation Oy, Mikkeli, Finland

[21] Appl. No.: 687,463

[22] PCT Filed: Jan. 30, 1995

[86] PCT No.: PCT/FI95/00044

§ 371 Date: Nov. 4, 1996

§ 102(e) Date: Nov. 4, 1996

[87] PCT Pub. No.: WO95/20758

PCT Pub. Date: Aug. 3, 1995

[30] Foreign Application Priority Data

Jan. 28, 1994 [FI] Finland ................. 940442

[51] Int. Cl.$^6$ .................................. G01N 21/00
[52] U.S. Cl. ................... 356/236; 356/446; 356/51; 250/228
[58] Field of Search ................... 356/446, 236, 356/51; 250/228

[56] References Cited

U.S. PATENT DOCUMENTS

| | | |
|---|---|---|
| 4,232,971 | 11/1980 | Suga . |
| 4,900,923 | 2/1990 | Gerlinger .................. 250/228 |
| 5,182,618 | 1/1993 | Heinonen .................. 250/228 |
| 5,384,641 | 1/1995 | Imura ...................... 250/228 |

FOREIGN PATENT DOCUMENTS

| | | |
|---|---|---|
| 0229602 | 7/1987 | European Pat. Off. . |
| 0293810 | 12/1988 | European Pat. Off. . |
| 0344645 | 12/1989 | European Pat. Off. . |
| 0569104 | 11/1993 | European Pat. Off. . |
| 1346766 | 2/1974 | United Kingdom . |
| 1 379 405 | 1/1975 | United Kingdom . |

*Primary Examiner*—Frank G. Font
*Assistant Examiner*—Jason D. Viena-Eisenberg
*Attorney, Agent, or Firm*—Merchant, Gould, Smith, Edell, Welter & Schmidt, P.A.

[57] ABSTRACT

A measuring instrument for reflectometric measurements, comprising a spherical measuring chamber (1) provided with a light source (2) and with a specimen aperture (3); a measuring channel (4) which has been provided with optics (5), with a photometer (6), with an optional stop (7) and with an optional filter (8); a reference channel (14) provided with optics (15), with a photometer (16), with an optional stop (17) and with an optional filter (18); and a signal processing and calculating device ($20_s$, $20_c$) for processing and comparing with each other the light intensity values observed by means of the photometers in the measuring and reference channels. As taught by the invention, the measuring instrument comprises at least one visible light light source ($2_s$) which emits substantially light having a wavelength mainly over about 380 nm, and a UV light source ($2_u$) which emits substantially light in the UV range having a wavelength mainly under about 380 nm, advantageously 300 to 380 nm.

8 Claims, 2 Drawing Sheets

MEASURING INSTRUMENT FOR REFLECTOMETRIC MEASUREMENTS

BACKGROUND OF THE INVENTION

The present invention concerns a measuring instrument for reflectometric measurements.

The invention specifically concerns a reflectometric measuring instrument in which the specimen under measurement is diffusely illuminated. In the literature this kind of method and apparatus is known under the name of ELREPHO (Electric Reflectance Photometer). Reflectometric measuring methods are employed when measuring the lightness, fluorescence, whiteness, translucence, opacity, brightness or other equivalent reflectometric optical properties of specimens. The invention quite particularly refers to a reflectometric measuring instrument intended to serve measurement of lightness of paper, cellulose and cardboard, i.e., of paper products.

At present, lightness of paper is in practice everywhere almost exclusively determined using a two-channel reflectometric measuring instrument manufactured by Zeiss. This instrument comprises a spherical measuring chamber, white inside, which is provided with two microscopes constituting a measuring channel and a reference channel. A standard specimen and/or the specimen to be measured is placed in the channel, and the light intensity of the object of measurement is detected with photometers disposed in the channels, and the detected light intensity values thus obtained are processed and, if necessary, amplified and compared with each other by means of a specific signal processing and calculating apparatus. The apparatus is calibrated with the aid of a standard specimen having a known reflectance value. The measuring method is in itself commonly known in the art and shall not be described in any greater detail in this connection; reference is made e.g. to the U.S. Pat. No. 07/793,261 and to the European Patent EP-229602.

However, the cited reflectometric instrument of prior art has proved unsatisfactory as the requirements of measuring accuracy have increased. Especially, when the aim is to regulate the illumination values of light sources, and thus the illumination of the measuring chamber e.g with the aid of a control stop, a situation is encountered in which the parts of the light produced by the light source (as a rule, white light) represented by various wavelengths, e.g. the proportion of UV light intensity to the intensity of visual light, will change owing to selectivity of the attenuator stop in different wavelength partial ranges. As a result, when the illumination of the measuring chamber is changed with the aid of the measuring stop, complete recalibration becomes necessary, to take taking the changed conditions into account. Furthermore, the results of measurement are no longer comparable with standard conditions, e.g. when the proportions of the light intensities of the UV range and the visible range change owing to attenuation. In other words, the measuring conditions fail to correspond to the standardized simulated daylight spectrum.

The problems just outlined have not been eliminated so far. These problems are particularly significant in connection with lightness measurements of paper products, and therefore the results of measurement obtained by the seller and receiver of paper often tend to differ, causing problems in the trade.

SUMMARY OF THE INVENTION

The object of the present invention is to eliminate the drawbacks that have been pointed out.

Specifically, the object of the invention is to disclose a measuring instrument for reflectometric measurements in which the illumination can be regulated in a desired manner so that the proportions of different wavelength ranges in the light used for illumination are constant or changed, as desired.

The invention is based on the idea that the measuring instrument comprises at least one source of visible light, emitting light which has a wavelength substantially over about 380 nm, and a source of UV light, emitting light in the UV range having a wavelength substantially under about 380 nm. The wavelength of the UV range emitted by the light source is preferably in the range 300 to 380 nm.

The visible light source may be, for instance, a conventional light source emitting white light, such as an incandescent lamp, a gas discharge lamp or an arc lamp, which has been provided with a particular filter for filtering off any light in the UV range.

The visible light source is further advantageously provided with a measuring stop for regulating the illumination of the measuring chamber.

The UV light source is suitably a UV lamp, or in general any light source whatsoever that emits UV light, for instance a light source which has been provided with a filter or prism for filtering off any light other than UV light. The UV light source may likewise be provided with a stop.

As a result of the invention, the light used to illuminate the measuring chamber, e.g. substantially white light, can be regulated to a given desired intensity level separately, independent of the UV light intensity level. Furthermore, the intensity of the light in the UV range used to illuminate the measuring chamber can be regulated to a given desired level independent of the intensity value of the visible light.

In general., regulation of the illuminating conditions of the measuring chamber can be implemented in a substantially more versatile manner, and in a desired manner, conforming to high requirements imposed e.g. by paper lightness measurement.

BRIEF DESCRIPTION OF THE DRAWINGS

The invention is described in detail in the following with the aid of embodiment examples, referring to the attached drawings, wherein.

DETAILED DESCRIPTION OF THE ILLUSTRATED EMBODIMENT

Figure 1:
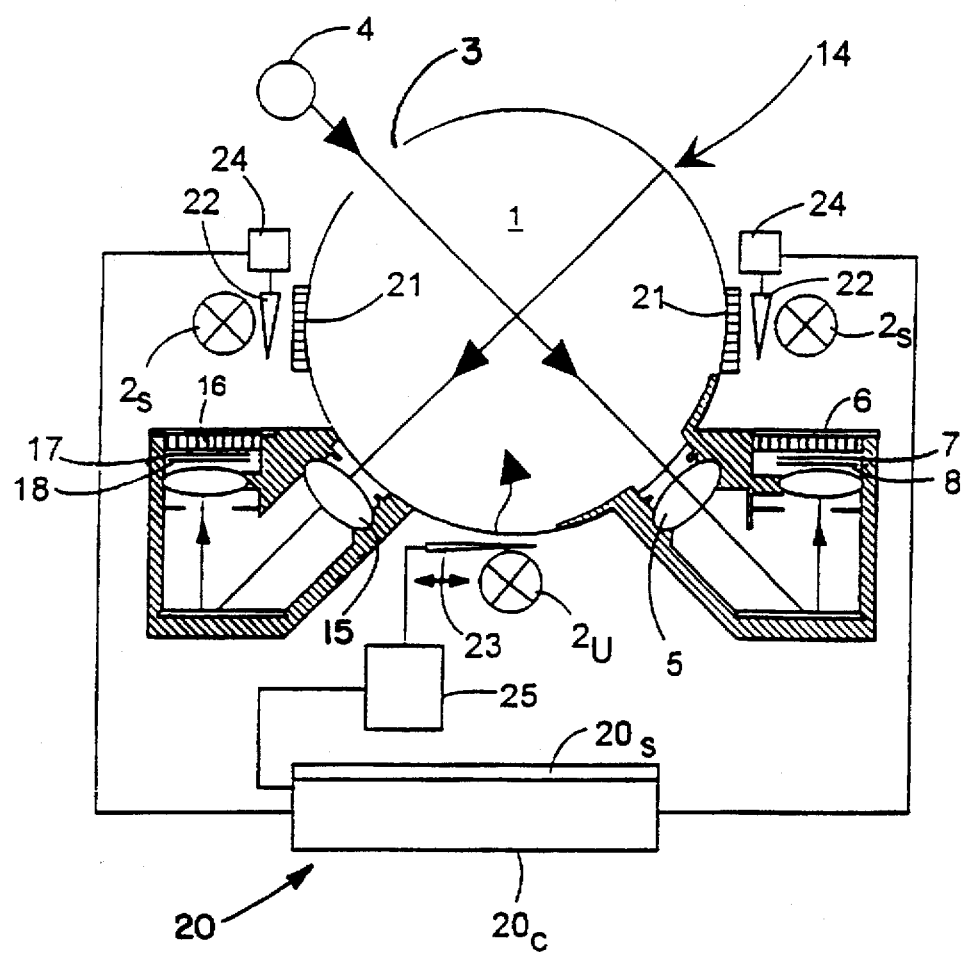
FIG. 1 presents a schematic drawing showing a measuring instrument for reflectometric measurements according to the invention, that is mainly for paper lightness measurements, and FIG. 2 displays the light intensity measured with an instrument as depicted in FIG. 1, plotted over wavelength, without and with an additional UV light source.

The measuring instrument comprises a spherical measuring chamber 1, provided with a light source $2_s$, represented in the present embodiment by two visible light sources $2_s$. The measuring chamber further comprises a specimen aperture 3, disposed so that the illumination of the specimen inserted in the specimen aperture will be diffuse. The measuring instrument further comprises a special measuring channel 4, provided with optics 5 for directing the light reflected by the specimen to a photometer 6 which is part of the measuring channel 4; the measuring channel 4 is further provided with an adjustable stop 7 for attenuating the light going to the photometer 6, and with a filter 8 for filtering the light going to the photometer 6. The measuring instrument further comprises a reference channel 14, provided with optics 15 for directing light from the measuring chamber to a photometer 16 which is part of the reference channel 14; the reference channel 14 is depicted in this embodiment has having an optional stop 17 for attenuation of the light going to the photometer 16, and with a filter 18 for filtering the light going to the photometer 16. The measuring instrument further comprises a signal processing and calculating device, such as an amplifier and other signal processing means, $20_s$, for processing, and amplifying, if desired the electric signal which is proportional to the intensity of the light beam directed to the photometers 6 and 16, and a calculating means $20_c$, such as a computer, for processing and comparing the light intensity values observed with the aid of the photometers 6 and 16 in the measuring channel 4 and in the reference channel 14, that is, the intensity values which said signals constitute.

As taught by the invention, the measuring instrument comprises at least one visible light source $2_s$, emitting light having a wavelength mainly greater than 380 nm, and a UV light source $2_u$, emitting light in the UV range having a wavelength mostly less than about 380 nm, advantageously in the range of approximately 300 to 380 nm.

The visible light light source $2_s$ is symmetrically placed with respect to the measuring channel 4 and the reference channel 14; the measuring channel 4 and reference channel 14 are so placed that their axes pass through the centre of the measuring chamber and form an angle a with each other, $\alpha>0°$ and $\alpha<180°$,. The UV light source $2_u$ is further symmetrically placed with respect to the visible light sources $2_s$ and to the measuring channel 4 and the reference channel 14.

The visible light light sources $2_s$ include a conventional lamp emitting white light and are additionally provided with filters 21 for filtering off any light of the UV range. Moreover, the visible light sources $2_s$ are provided with measuring stops 22 for regulating the intensity of the visible light. The UV light source $2_u$ is furthermore provided with a stop 23 for regulating the intensity of the UV light.

The measuring stops of the visible light sources $2_s$ are provided with a drive means 24, adjustment of the which takes place under control of the calculating device 20. The corresponding adjustment of the stop associated with the UV light source $2_u$ is provided with a drive means 25, controlled by the computer $20_c$.

In the embodiment presented, nothing else has been described but the adjustment of illumination in the measuring chamber of the measuring instrument; the measurement is accomplished in a way known in itself in the art, as is extensively documented in the literature. Furthermore, the measuring instrument of the invention, and especially the regulation of illumination in the measuring chamber, is appropriate to be employed in connection with any reflectometric measuring instrument whatsoever.

Figure 2:
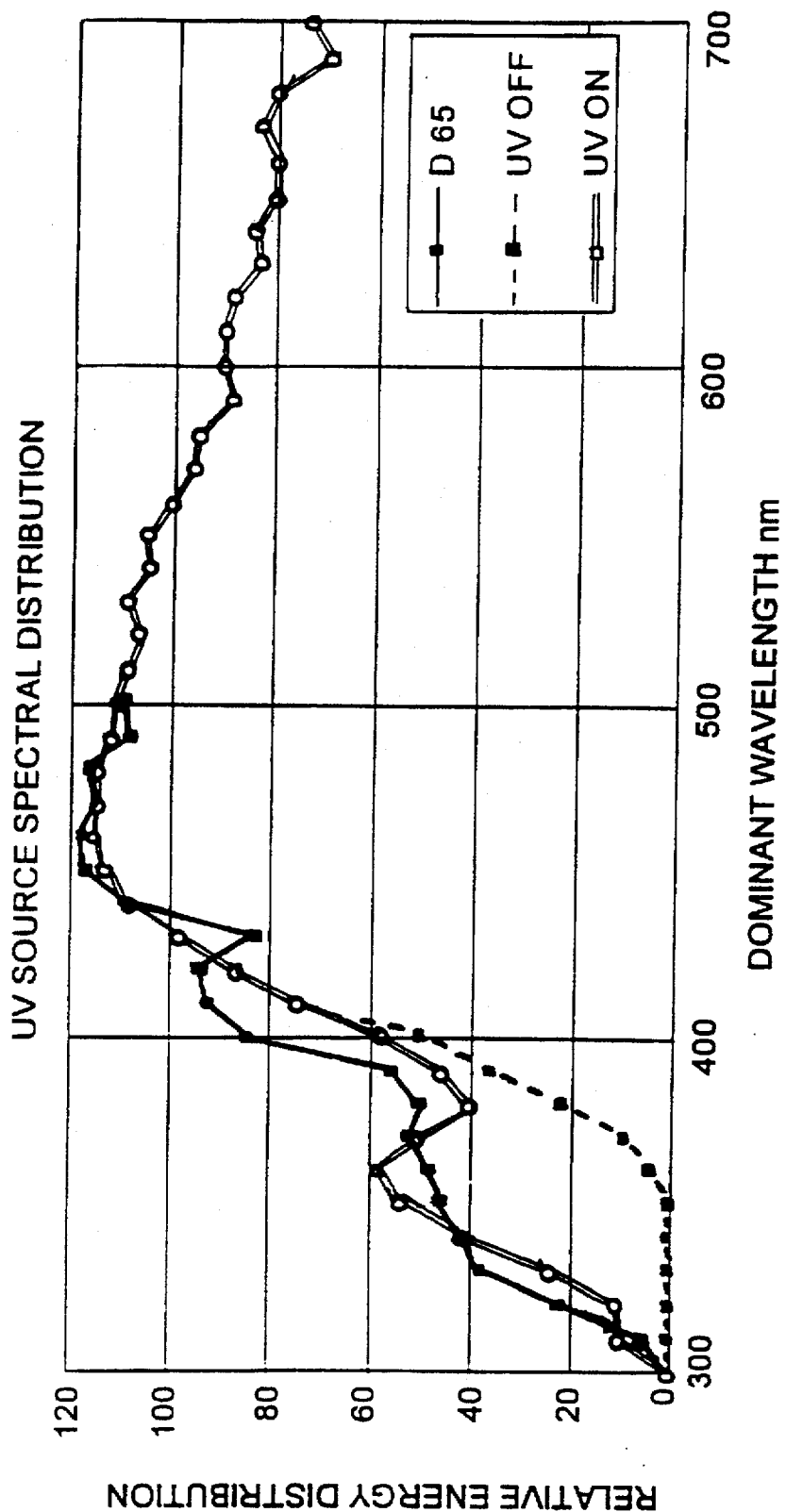

FIG. 2 schematically illustrates the measuring chamber illumination determined in a measuring instrument according to the invention, plotted against wavelength, when two light sources emitting visible light only are used; the respective graph has been labelled UV OFF. The figure further displays the corresponding graph obtained when for illumination of the measuring chamber there has in addition been used a UV light source emitting substantially light of the UV range, with wavelength mainly between 300 and 380 nm; this curve is labelled UV ON.

Examination of FIG. 2 reveals that the measuring instrument of the invention conforms well to the values of illumination simulating daylight, including the UV range. As shown, the spectrum produced is in close agreement with the D 65 standard.

The embodiment examples are merely meant to illustrate the invention, without in any way restricting it.

I claim:

1. A measuring instrument for reflectometric measurements of a specimen, comprising:

a spherical measuring chamber provided with a specimen aperture so that illumination of the specimen placed in said specimen aperture is diffuse;

at least two light sources, including a first visible light source substantially emitting light having a wavelength greater than about 380 nm, and a UV light source substantially emitting light having a wavelength less than about 380 nm, the UV source being provided with an attenuating stop so that UV light intensity is independently controllable of visible light intensity;

a measuring channel provided with optics and a first photometer, to direct light reflected by the specimen to the first photometer;

a reference channel provided with optics and a second photometer to direct light from the measuring chamber to the second photometer; and a signal processing and calculating device for processing and comparing light intensity values observed by the first and second photometers.

2. Measuring instrument according to claim 1, further comprising a second visible light source substantially emitting light having a wavelength over about 380 nm.

3. Measuring instrument according to claim 2, wherein the visible light sources are each provided with a filter to filter out light in the UV range having a wavelength under 380 nm.

4. Measuring instrument according to claim 1, wherein the visible light source comprises an adjustable stop controllable by the signal processing and calculating device.

5. Measuring instrument according to claim 1, wherein the attenuating stop of the UV light source is controllable by the signal processing and calculating device.

6. Measuring instrument according to claim 1, wherein the measuring channel is provided with an attenuating stop to attenuate light entering the first photometer, and a filter to filter light entering the first photometer.

7. Measuring instrument according to claim 1, wherein the UV source substantially emits light ranging from 300 to 380 nm.

8. Measuring instrument according to claim 1, wherein the reference channel is provided with an attenuating stop to attenuate light entering the second photometer, and a filter to filter light entering the second photometer.

* * * * *